United States Patent [19]

Sandler et al.

[11] 4,356,274

[45] Oct. 26, 1982

[54] SMOKE SUPPRESSED RIGID POLYURETHANE FOAM

[75] Inventors: Stanley R. Sandler, Springfield; Jeffrey D. Miano, Norristown, both of Pa.

[73] Assignee: Pennwalt Corporation, Philadelphia, Pa.

[21] Appl. No.: 30,400

[22] Filed: Apr. 16, 1979

Related U.S. Application Data

[63] Continuation of Ser. No. 897,617, Apr. 19, 1978, abandoned.

[51] Int. Cl.$^3$ .............................................. C12P 17/14
[52] U.S. Cl. ..................... 521/120; 521/114; 521/121; 521/124; 521/126; 521/128; 521/155; 521/89; 521/903; 524/95; 524/106; 524/83; 524/100; 524/93; 524/202; 524/330
[58] Field of Search ............... 260/45.75 S, 45.75 J, 260/45.75 C, 45.75 W, 45.75 B, 45.75 R, 45.75 G, 45.75 P, 45.75 M, 45.75 N, 45.8 RW, 45.8 NT, 45.8 NZ, 45.8 N, 45.8 SN, 45.9 R, 45.95 C, 45.7 S; 521/114, 121, 120, 124, 126, 128, 155, 903, 89

[56] References Cited

U.S. PATENT DOCUMENTS

| | | | |
|---|---|---|---|
| 3,006,870 | 10/1961 | Steinfatt et al. | 521/121 |
| 3,245,923 | 4/1966 | Manzella et al. | 521/120 |
| 3,255,129 | 6/1966 | Ferrari | 521/120 |
| 3,432,474 | 3/1969 | Lombardi | 528/52 |
| 3,620,985 | 11/1971 | Larkin et al. | 521/124 |
| 3,876,567 | 4/1975 | Larkin et al. | 521/121 |
| 3,956,236 | 5/1976 | Evans et al. | 260/45.85 T |
| 3,978,011 | 8/1976 | Molbert | 521/121 |
| 4,011,194 | 3/1977 | Sandler | 260/45.75 C |
| 4,018,724 | 4/1977 | Cobbledich | 521/121 |

*Primary Examiner*—Melvyn I. Marquis

[57] ABSTRACT

Smoke suppressed rigid polyurethane foams are prepared from a reaction mixture comprising as the smoke suppressant additive a metal salt of a: dialkyl dithiocarbamate, a mercaptobenzothiazole, a 2,5-dimercapto-1,3,4-thiadiazole, a mercaptotriazine, a hydroxy thiophenol or an aliphatic dimercapto compound of 2 to 10 carbons.

6 Claims, No Drawings

SMOKE SUPPRESSED RIGID POLYURETHANE FOAM

This is a continuation of application Ser. No. 897,617, filed Apr. 19, 1978, now abandoned.

BACKGROUND OF THE INVENTION

1. Field of the Invention

This invention relates to smoke suppressed rigid polyurethane foam composition. More specifically, this invention relates to the addition of organic sulfur-containing metal compounds to rigid polyurethane foam compositions to reduce the smoke generated on burning the resulting foams.

2. Description of the Prior Art

Rigid foams are becoming increasingly important as an insulation material in construction of new buildings to reduce energy losses. At the same time, building code agencies are requiring lower levels of smoke to be generated when foam burns in order to make the exits easily observable to facilitate access by firemen and the escape of occupants.

Prior to the instant invention polyurethane foams could be smoke suppressed by using sulfur containing compounds such as elemental sulfur or certain organosulfur compounds such as di-t-butyl polysulfide and ethylene trithiocarbonate. The use of these materials is illustrated in U.S. Pat. Nos. 3,542,701, 3,876,568, and 3,933,694. These organosulfur compounds have the disadvantage of either being too volatile or imparting an objectionable odor during processing. Polyurethane foam containing these prior art sulfur compounds still produced substantial amounts of smoke.

The compounds used in the rigid foam compositions of the present invention overcome the disadvantages of the prior art because they substantially reduce the amount of smoke produced from burning polyurethane. This has been demonstrated in the Examples, infra.

STATEMENT OF THE INVENTION

The present invention is directed to a smoke suppressed rigid polyurethane foam prepared from a reaction mixture which comprises a smoke suppressing amount of a compound selected from the group consisting of:

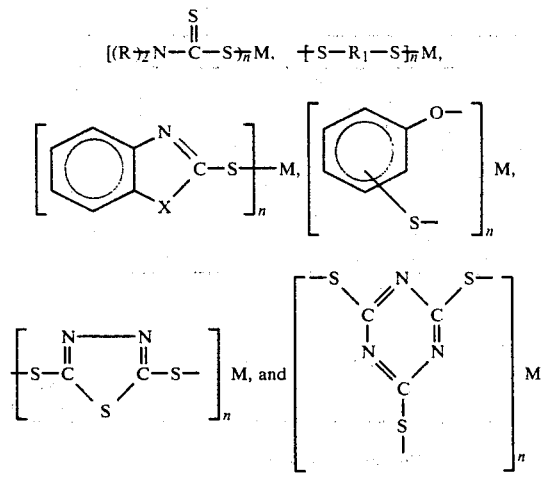

wherein:

R is a lower alkyl of 1 to 5 carbons;
$R_1$ is a cycloalkyl of 3–10 carbons or an alkyl of 2–10 carbons;
n is an integer equal to the valence of M; and
X is selected from S, O or NH.
M is selected from the group consisting of copper, zinc, aluminum, tin, antimony, bismuth, vanadium, chromium, molybdenum, manganese, iron, cobalt, and nickel.

DETAILED DESCRIPTION OF THE INVENTION

The present invention is directed to a smoke suppressed, rigid polyurethane foam. Generally, polyurethanes are prepared by the reaction of toluene diisocyanate or polymethylene polyphenylisocyanate or mixture thereof with polyfunctional hydroxy compounds. Some typical examples of rigid polyurethane foams are described in E. N. Doyle "The Development and Use of Polyurethane Products", McGraw-Hill Book Co., New York, 1971 and in W. C. Kuryla and A. J. Papa, "Flame Retardancy of Polymeric Materials", Volume 3, Marcel Dekker, Inc., New York, 1975. The rigid polyurethane resins of this invention may also contain flame retardants such as chloroethyl phosphates, phosphorous-nitrogen compounds, and brominated or chlorinated polyols.

The smoke suppressant additives used to prepare the rigid polyurethane foams of this invention may be prepared by the reaction of salts of metals selected from copper, zinc, aluminum, tin, antimony, bismuth, vanadium, chromium, molybdenum, manganese, iron, cobalt, and nickel with the sodium salts of sulfur containing compounds selected from mercaptobenzothiazoles, 2,5-di-mercapto-1,3,4-thiadiazoles, mercaptotriazines, dialkyl dithiocarbamates, hydroxy thiophenols and aliphatic dimercapto compounds having 2 to 10 carbons. These additives are either monomeric or polymeric salts and can be cyclic or linear; they are physically mixed with the reactants for preparing the polyurethane foam in the amount of 0.1 to 20 parts by weight of the formulation of reactants (i.e., polyols, surfactants, catalysts, water, blowing agents, flame retardant, and isocyanate) to give the polyurethane foam.

Representative smoke suppressant additives used in this invention are as follows:
ferrous 2-mercaptobenzothiazole
cupric 2-mercaptobenzothiazole
zinc 2-mercaptobenzothiazole
ferrous dimethyl dithiocarbamate
cupric dimethyl dithiocarbamate
zinc dimethyl dithiocarbamate
ferrous dibutyl dithiocarbamate
cupric dibutyl dithiocarbamate
zinc dibutyl dithiocarbamate
nickelous dibutyl dithiocarbamate
antimonous dibutyl dithiocarbamate
ferrous dimercapto-1,3,4-dithiadiazole
cupric dimercapto-1,3,4-dithiadiazole
zinc dimercapto-1,3,4-dithiadiazole
ferrous salt of p-hydroxythiophenol
zinc salt of p-hydroxythiophenol
ferrous 2-mercaptobenzoxazole
ferrous 2-mercaptobenzimidazole
zinc salt of trimercaptotriazine
ferrous salt of 1,6-dimercaptohexane
cupric salt of 1,6-dimercaptohexane
cobaltous dimethyl dithiocarbamate nickelous dimethyl dithiocarbamate
stannous 2-mercaptobenzothiazole In the practice of this invention, preferred metals used for the smoke suppressants are iron, copper, and zinc.

The preferred organosulfur compounds used to prepare the metal salts are selected from mercaptobenzothiazoles, dimercapto-1,3,4-thiadiazoles, and dialkyl dithiocarbamates.

The preferred smoke suppressants are: ferrous 2-mercaptobenzothiazole, ferrous dimethyl dithiocarbamate, ferrous 2,5-dimercapto-1,3,4-thiadiazole, cupric 2-mercaptobenzothiazole, cupric dimethyl dithiocarbamate, cupric 2,5-dimercapto-1,3,4-thiadiazole, zinc 2-mercaptobenzothiazole, zinc dimethyl dithiocarbamate, zinc dibutyl dithiocarbamate, and zinc 2,5-dimercapto 1,3,4-thiadiazole.

The following examples illustrate the present invention but are not intended to limit the invention thereto.

Rigid polyurethane foams described in the following examples are prepared by stirring the smoke suppressant additive with the polyol followed by addition of catalysts, surfactant, water and/or blowing agent and isocyanate as described by K. C. Frisch and S. L. Reegan in "Advances in Urethane Science and Technology", Volumes 1 to 4, Technomic, Conn., 1971–1976. The rigid foams are made by pouring the stirred reaction mixture into an 8"×8"×5" box. The foam is aged for seven days, and then cut into 3"×3"×1" specimens that are burned in the NBS smoke chamber using the flaming mode in accordance with ASTM Special Technical Publication 422 (1969) and NFPA 258-T, "Smoke Generated by Solid Materials", May 1974. The average of two or more values is reported.

Example 1 shows that a rigid polyurethane foam containing a phosphorus based flame retardant and no smoke suppressant produces a large quantity of smoke ($D_{mc}=355$).

Examples 2–5 show that rigid polyurethane foams of the same formulation as Example 1 but containing metal dialkyldithiocarbamates or zinc mercaptobenzothiazole produce less smoke than a foam containing prior art elemental sulfur at the same loading level by weight.

EXAMPLES 1–5

| Recipe: | Parts |
|---|---|
| Polyol - Pluracol 383 (BASF Wyandotte)[a] | 100.0 |
| Surfactant - DC - 193 (Dow Corning)[b] | 1.0 |
| Dimethylaminoethanol (Pennwalt) | 2.94 |
| Dibutyltin Dilaurate (M & T) | 0.06 |
| Water | 0.9 |
| Blowing Agent - Isotron 11 (Pennwalt)[c] | 50.0 |
| Flame Retardant - Fyrol 6 (Stauffer)[d] | 35.0 |
| Isocyanate - PAPI (Upjohn)[e] | 182.0 |
| Smoke Suppressant | as shown below |

[a]Sucrose - based polyol, OH number = 483, contains <1% phosphorus
[b]Silicone surfactant
[c]Fluorocarbon 11
[d]Diethyl N,N—Bis(2-hydroxyethyl)aminomethylphosphonate
[e]Polymethylene polyphenylisocyanate, NCO equivalent = 133

| Example # | Smoke Suppressant | pph | $D_{mc}$ | % Smoke Reduction |
|---|---|---|---|---|
| 1 | None | — | 355 | 0 |
| 2 | Sulfur | 20 | 266 | 25 |
| 3 | Ferrous 2-mercaptobenzothiazole | 20 | 216 | 39 |
| 4 | Zinc dimethyl dithiocarbamate | 20 | 143 | 60 |
| 5 | Zinc 2,5-dimercapto-1,3,4-thiadiazole | 20 | 135 | 62 |

Examples 6–10 show that rigid polyurethane foams flame retarded with an organobromine compound and containing the metal organo sulfur compounds of this invention produce less smoke than a foam containing prior art elemental sulfur at the same percent sulfur content.

EXAMPLES 6–10

| Recipe: | Parts |
|---|---|
| Polyol - Pluracol 383 (BASF Wyandotte)[a] | 100.0 |
| Surfactant - DC - 193 (Dow Corning)[b] | 1.0 |
| Dimethylaminoethanol | 2.94 |
| Dibutyltin Dilaurate | 0.06 |
| Water | 0.9 |
| Blowing Agent - Isotron 11 (Pennwalt)[c] | 50.0 |
| Flame Retardant - FR - 1138 (DOW)[d] | 30.0 |
| Isocyanate - PAPI (Upjohn)[e] | 173.0 |
| Smoke Suppressant | as shown below |

[a]Sucrose based polyol, OH number = 483, contains <1% phosphorus
[b]Silicone surfactant
[c]Fluorocarbon 11
[d]Dibromoneopentyl glycol
[e]Polymethylene polyphenylisocyanate, NCO equivalent = 133

| Example # | Smoke Suppressant | pph* | $D_{mc}$ | % Smoke Reduction |
|---|---|---|---|---|
| 6 | None | — | 344 | 0 |
| 7 | Sulfur | 8.1 | 264 | 23 |
| 8 | Ferrous dimethyl dithiocarbamate | 20.1 | 163 | 53 |
| 9 | Zinc dimethyl dithiocarbamate | 20.8 | 179 | 48 |
| 10 | Cupric dimethyl dithiocarbamate | 20.4 | 194 | 44 |

*All present at the same percent sulfur by weight.

Examples 11–12 are presented to show the effectiveness of zinc dimethyl dithiocarbamate as a smoke suppressant for rigid polyurethane containing a chlorinated flame retardant (Thermolin RF230). This metal sulfur-containing salt was earlier shown in Example 4 to also be effective as a smoke suppressant for rigid polyurethane foam containing a phosphorus/nitrogen flame retardant (Fryol 6).

EXAMPLES 11–13

| Preparation of Sample | Parts |
|---|---|
| Polyol - Thernolin RF230 (Olin)[a] | 25.0 |
| Polyol - Pluracol 383 (BASF Wyandotte)[b] | 75.0 |
| Surfactant - DC - 193 (Dow Corning)[c] | 1.0 |
| Dimethylaminoethanol | 2.94 |
| Dibutyltin Dilaurate | 0.06 |
| Water | 0.9 |
| Blowing Agent - Isotron 11 (Pennwalt)[d] | 50.0 |
| Isocyanate - PAPI (Upjohn)[e] | 132.4 |
| Smoke Suppressant | as shown below |

[a]Hydroxyl number = 365, 47% chlorine
[b]Sucrose based polyol, OH number = 483, contains <1% phosphorus
[c]Silicone surfactant
[d]Fluorocarbon 11
[e]Polymethylene polyphenylisocyanate, NCO equivalent = 133

| Example # | Smoke Suppressant | phr | $D_{mc}$ | % Smoke Reduction |
|---|---|---|---|---|
| 11 | None | — | 220 | 0 |
| 12 | Zinc dimethyl dithiocarbamate | 11.6 | 136 | 38 |

EXAMPLE 13

To a rigid polyurethane recipe as described in Examples 11–12 is added 11.6 pph of zinc dibutyl dithiocarbamate $Zn[(C_4H_9)_2NCS_2]_2$ (Pennwalt's Butyl Ziram). The resulting rigid polyurethane foam on combustion gave smoke reductions on the order of about 38% or about the same as that from zinc dimethyl dithiocarbamate shown in Example 12.

EXAMPLE 14

Preparation of Zinc 2,5-Dimercapto-1,3,4-thiadiazole 2,5 dimercapto 1,3,4-thiadiazole (50 g, 0.33 mole) is stirred in 100 ml H₂O. NaOH (26.7 g 0.66 mole) is slowly added with stirring and cooling. A ZnCl₂ solution (45.4 g, 0.33 mole dissolved in 300 ml H₂O) is added to the sodium dimercapto-1,3,4-thiadiazole salt solution resulting in the formation of a white precipitate. The precipitate is filtered and dried to give a quantitative yield of zinc 2,5-dimercapto-1,3,4-thiadiazole.

Elemental and spectroscopic analyses are consistent with the assigned structure.

EXAMPLE 15

Preparation of Zinc Dimethyl Dithiocarbamate

Sodium dimethyl dithiocarbamate (75.2 g, 0.66 mole) is dissolved in 100 ml H₂O. A ZnCl₂ solution (45.4 g, 0.33 mole dissolved in 300 ml H₂O) is added to the sodium dimethyl dithiocarbamate solution. Immediately, a white precipitate forms which is filtered and dried to give a quantitative yield of zinc dimethyl dithiocarbamate.

Elemental and spectroscopic analyses are consistent with the assigned structure as being:

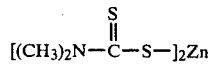

EXAMPLE 16

Preparation of Cupric Dimethyl Dithiocarbamate

Sodium dimethyl dithiocarbamate (75.2 g, 0.66 mole) is dissolved in 100 ml H₂O. A CuCl₂ solution (44.3 g, 0.33 mole dissolved in 300 ml H₂O) is added to the sodium dimethyl dithiocarbamate solution. Immediately, a precipitate forms which is filtered and dried to give a quantitative yield of cupric dimethyl dithiocarbamate.

Elemental and spectroscopic analyses are consistent with the assigned structure as being:

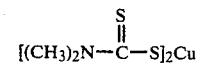

What is claimed:

1. A rigid polyurethane foam prepared from a reaction mixture which includes a smoke suppressing amount of a compound selected from the group consisting of ferrous 2-mercaptobenzothiazole, cupric 2-mercaptobenzothiazole, ferrous 2,5-dimercapto-1,3,4-thiadiazole, cupric 2,5-dimercapto-1,3,4-thiadiazole, and zinc 2,5-dimercapto-1,3,4-thiadiazole.

2. The polyurethane foam of claim 1 wherein the compound is ferrous 2-mercaptobenzothiazole.

3. The polyurethane foam of claim 1 wherein the compound is zinc 2,5-dimercapto-1,3,4-thiadiazole.

4. The polyurethane foam of claim 1 wherein the compound is ferrous 2,5-dimercapto 1,3,4-thiadiazole.

5. The polyurethane foam of claim 1 wherein the compound is cupric 2-mercaptobenzothiazole.

6. The polyurethane foam of claim 1 wherein the compound is cupric 2,5-dimercapto-1,3,4-thiadiazole.

* * * * *